(12) United States Patent
Mak et al.

(10) Patent No.: US 10,952,617 B2
(45) Date of Patent: Mar. 23, 2021

(54) MICROMETER SIZE MULTI-FUNCTIONAL PROBE FOR OCT AND ELECTRO-PHYSIOLOGICAL RECORDING

(71) Applicant: SYNAPTIVE MEDICAL INC., Toronto (CA)

(72) Inventors: Siu Wai Jacky Mak, Toronto (CA); Fangxin Li, Toronto (CA)

(73) Assignee: SYNAPTIVE MEDICAL INC., Toronto (CA)

(*) Notice: Subject to any disclaimer, the term of this patent is extended or adjusted under 35 U.S.C. 154(b) by 0 days.

(21) Appl. No.: 16/434,475

(22) Filed: Jun. 7, 2019

(65) Prior Publication Data

US 2019/0365232 A1 Dec. 5, 2019

Related U.S. Application Data

(63) Continuation of application No. 15/573,247, filed as application No. PCT/IB2016/056145 on Oct. 14, 2016, now Pat. No. 10,362,942.

(51) Int. Cl.
| | |
|---|---|
| A61B 5/00 | (2006.01) |
| A61B 5/0478 | (2006.01) |
| A61B 5/06 | (2006.01) |
| A61B 3/00 | (2006.01) |
| A61B 3/10 | (2006.01) |

(52) U.S. Cl.
CPC .............. *A61B 5/0066* (2013.01); *A61B 3/00* (2013.01); *A61B 3/10* (2013.01); *A61B 5/0042* (2013.01); *A61B 5/0086* (2013.01); *A61B 5/0478* (2013.01); *A61B 5/065* (2013.01)

(58) Field of Classification Search
None
See application file for complete search history.

(56) References Cited

U.S. PATENT DOCUMENTS

| | | | |
|---|---|---|---|
| 2005/0148836 A1* | 7/2005 | Kleen | A61B 18/1492 600/374 |
| 2013/0223702 A1* | 8/2013 | Holsing | A61B 6/12 382/128 |
| 2014/0121648 A1* | 5/2014 | Weiss | B29C 70/52 604/528 |
| 2016/0235480 A1* | 8/2016 | Scholl | A61B 17/7086 |
| 2016/0287307 A1* | 10/2016 | Clark | A61B 5/6852 |
| 2017/0122928 A1* | 5/2017 | Naughton | A61B 5/4058 |
| 2017/0213013 A1* | 7/2017 | Piron | G16H 30/40 |
| 2017/0265947 A1* | 9/2017 | Dyer | G16H 40/63 |
| 2018/0271491 A1* | 9/2018 | Flanagan | A61B 5/0097 |
| 2018/0272042 A1* | 9/2018 | Borton | A61F 2/0077 |

* cited by examiner

*Primary Examiner* — Shawn Decenzo

(57) ABSTRACT

A device and method for guided insertion of microelectrodes into tissue is provided. The device includes a flexible optical fiber for optical coherence tomography imaging, a metal layer coating the optical fiber for recording electrical signals and an outer insulation layer coating the metal layer along the optical fiber length. The method includes inserting an optical fiber coated with a metal layer and further coated with an insulation layer into a tissue, collecting intraoperative image data through the optical fiber by optical coherence tomography, receiving the image data on a computer and displaying the image on a monitor, using the image data to determine a location in the tissue, receiving an electrical nerve signal through the metal layer and measuring the electrical nerve signal on a electrophysiological recording system.

14 Claims, 9 Drawing Sheets

MICROMETER SIZE MULTI-FUNCTIONAL PROBE FOR OCT AND ELECTRO-PHYSIOLOGICAL RECORDING

CROSS-REFERENCE TO RELATED APPLICATION(S)

This application is a continuation application, claiming priority, and the benefit of, U.S. patent application Ser. No. 15/573,247, filed on Nov. 10, 2017, which is a national stage entry application of International Patent Application No. PCT/162016/056145, filed on Oct. 14, 2016, both all of which are incorporated herein by reference in their entirety.

TECHNICAL FIELD

The present disclosure relates to a device for electrophysiological recording and more specifically to a device for navigating electrophysiological recording.

BACKGROUND

Deep Brain Stimulation (DBS) is a surgical procedure used for the treatment of various diseases including Parkinson's disease and essential tremor. In the surgical procedure, a DBS lead is implanted at a target site to stimulate brain matter and thereby alleviate the clinical condition. To be effective and avoid deleterious side effects, the DBS lead must be located correctly within the brain matter. Therefore, before DBS lead placement is made, microelectrodes are typically used to penetrate deep brain matter and refine anatomical or imaging-based stereotactic targeting techniques. The microelectrode recording is used to precisely identify the target (i.e. thalamus, sub-thalamic nuclei (STN), GPi) in the brain for test stimulation before DBS lead placement is made. This recording involves a small metal wire, namely the microelectrodes recording leads (MER lead) that monitors the activity of nerve cells in the target area. Through the recording, the surgeon listens to the contrast in the electrical signal fired by the neurons and reads the waveforms on a computer to identify the stimulation target. The size of the MER lead is made extremely small to prevent bleeding and damage to the human brain as it is inserted deep into the human brain.

Currently, MER leads and stereotactic image guided systems (e.g. Nexframe® stereotactic image guided system by Medtronics) are the only tool the surgeon uses to locate the stimulation target. Intraoperative CT scans to augment information provided by preoperative MRI scans have been put forward to provide more accurate navigation of the MER. However, no intra-operative imaging device is currently available to provide real time images to the surgeon. In addition, the target for stimulation is typically very small (eg. for STN 3 to 5 mm), which makes it difficult to locate if the brain shifts during surgery. If the initial path of the MER lead is offset such that the stimulation target is missed, the surgeon will typically pull back the lead and reinsert it a few millimeters away with no indication or guidance from any devices on what direction and distance to re-target the lead. This method is suboptimal and can cause significant damage to the brain. Reinserting the probe multiple times into a similar region of the brain causes increasing risk of excessive bleeding which causes brain damage as well as affecting stimulation effectiveness.

SUMMARY

An object of the present invention is to provide a device and method for guided insertion of microelectrodes into tissue.

Thus by one broad aspect of the present invention, a probe for tissue recording in a medical procedure is provided, the probe including a flexible optical fiber for optical coherence tomography imaging, having an optical fiber distal end and an optical fiber proximal end, a metal layer coating the optical fiber length for recording electrical signals, having a corresponding metal layer distal end and a corresponding metal layer proximal end; and an outer insulation layer coating the metal layer along the optical fiber length.

By another broad aspect of the present invention, a method for measuring electrical nerve signals in a tissue is provided, the method comprising inserting a probe having an optical fiber coated with a metal layer and further coated with an insulation layer into a tissue, collecting intraoperative image data through the optical fiber by optical coherence tomography, receiving the image data on a computer and displaying the image on a monitor, using the image data to determine a location in the tissue, receiving an electrical nerve signal through the metal layer and measuring the electrical nerve signal on a electrophysiological recording system.

A further understanding of the functional and advantageous aspects of the disclosure can be realized by reference to the following detailed description and drawings.

DETAILED DESCRIPTION

Figure 1:
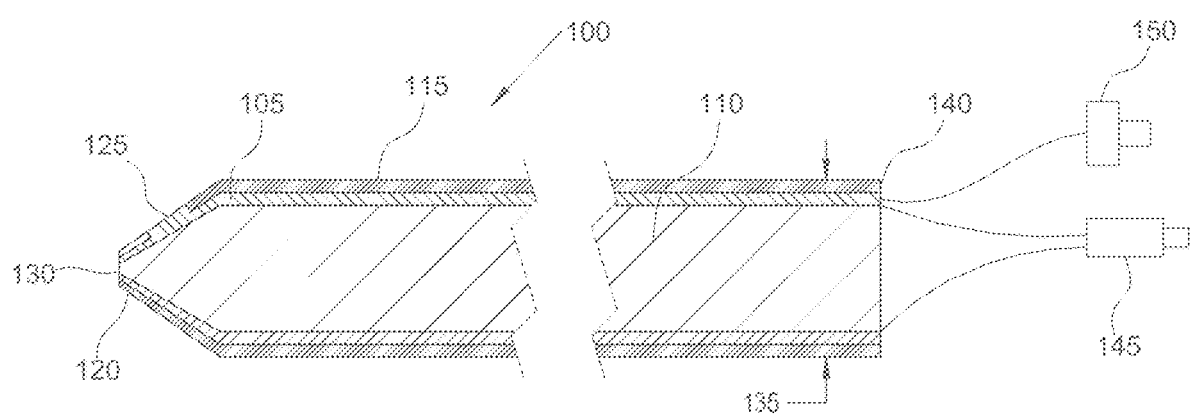
FIG. 1 illustrates a cross sectional view of an embodiment of the present invention.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

Unless defined otherwise, all technical and scientific terms used herein are intended to have the same meaning as commonly understood to one of ordinary skill in the art.

Unless otherwise indicated, such as through context, as used herein, the following terms are intended to have the following meanings:

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Several embodiments of the present disclosure seek to address the aforementioned inadequacies of existing devices and methods to support surgical procedures utilizing surgical tools.

The present invention discloses an ultra-miniature probe that enables high resolution imaging for a DBS procedure using Optical Coherence Tomography (OCT) with a probe diameter similar to an MER lead (<350 microns). In addition, the probe can be used for simultaneous microelectrode recording and stimulation.

Referring to FIG. 1, a probe 100 described here includes a metal coated optical fiber in which the metal coating 105 is utilized for microelectrode recording and the optical fiber center 110 is utilized for OCT imaging. OCT is a noninvasive imaging technique providing microscopic sectioning of biological tissues. The metal coating 105 allows electrical signals for microelectrode recording and tissue stimulation, and enables the fiber to be sterilizable. The metal coating 105 is further coated with insulation 115 along the length of the probe 100, but the insulation coating 115 is discontinuous near the probe distal end 120, thereby providing tissue contact 125 for electro-physiological recording. The optical fiber tip 130 at the probe distal end 120 is used for OCT imaging and is not coated with metal or insulation. The diameter 135 of the probe 100 is optimally less than 300 microns, although in alternate embodiments the probe may be less than 700 microns. On the proximal end 140 of the probe 100, the metal-coated optical fiber is split into an optical connector 145 for connection to an OCT system, and an electrical connector 150 for connection to an electrophysiological recording system. OCT images are generated as the probe penetrates through the brain by manual insertion. Furthermore, three-dimensional images may be formed if the probe is slowly spun around its longitudinal axis. For this purpose, a mechanical device may be attached to the probe to translate and rotate the probe to form two-dimensional and three-dimensional OCT images.

The probe 100 combines OCT (optical coherence tomography) imaging with an electrical probe, to integrate the electrical system with an optical imaging system and thereby provide an ultra miniature probe for high resolution imaging, for example in deep brain stimulation. The optical imaging may be used to monitor insertion of the probe into brain matter, thereby providing a more informed insertion toward the target tissue. OCT contrast can be used to provide update registration of the probe position dynamically intraoperatively. OCT contrast may also provide micro-vasculature information, thereby reducing the risk of vessel damage and bleeding, and can assist in direction for lead reinsertion when the target is missed. The metal-coated optical fiber allows simultaneous microelectrode recording and tissue stimulation. OCT and polarization sensitive OCT (PS-OCT) can also provide contrast between white and grey matters in the brain enabling fiber tracts in the brain to be used as local landmarks to help targeting in addition to structural contrast in the brain tissue. For example, STN is surrounded by white matter which enables OCT to be used to help target the exact location of STN in addition to MER.

Figure 2:
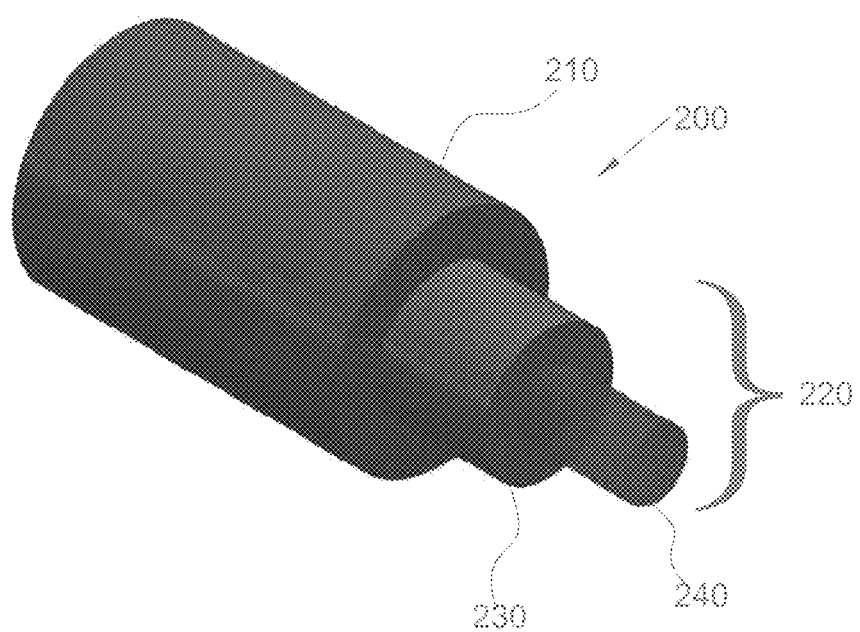
FIG. 2 illustrates a transverse view of an embodiment of the present invention.

Referring to FIG. 2, a metal coated fiber structure 200, with metal coating 210 surrounding the length of an optical fiber core 220 (comprising pure fused silica cladding and a germanium doped silica core), without insulation coating is shown. On the distal end of the optical fiber 230, the fiber tip 240 is shaped in a way to focus infrared (IR) light for OCT imaging and an opening through the insulation layer (not shown) to the metal coating is created to allow tissue contact for electro-physiological recording.

Figure 3:
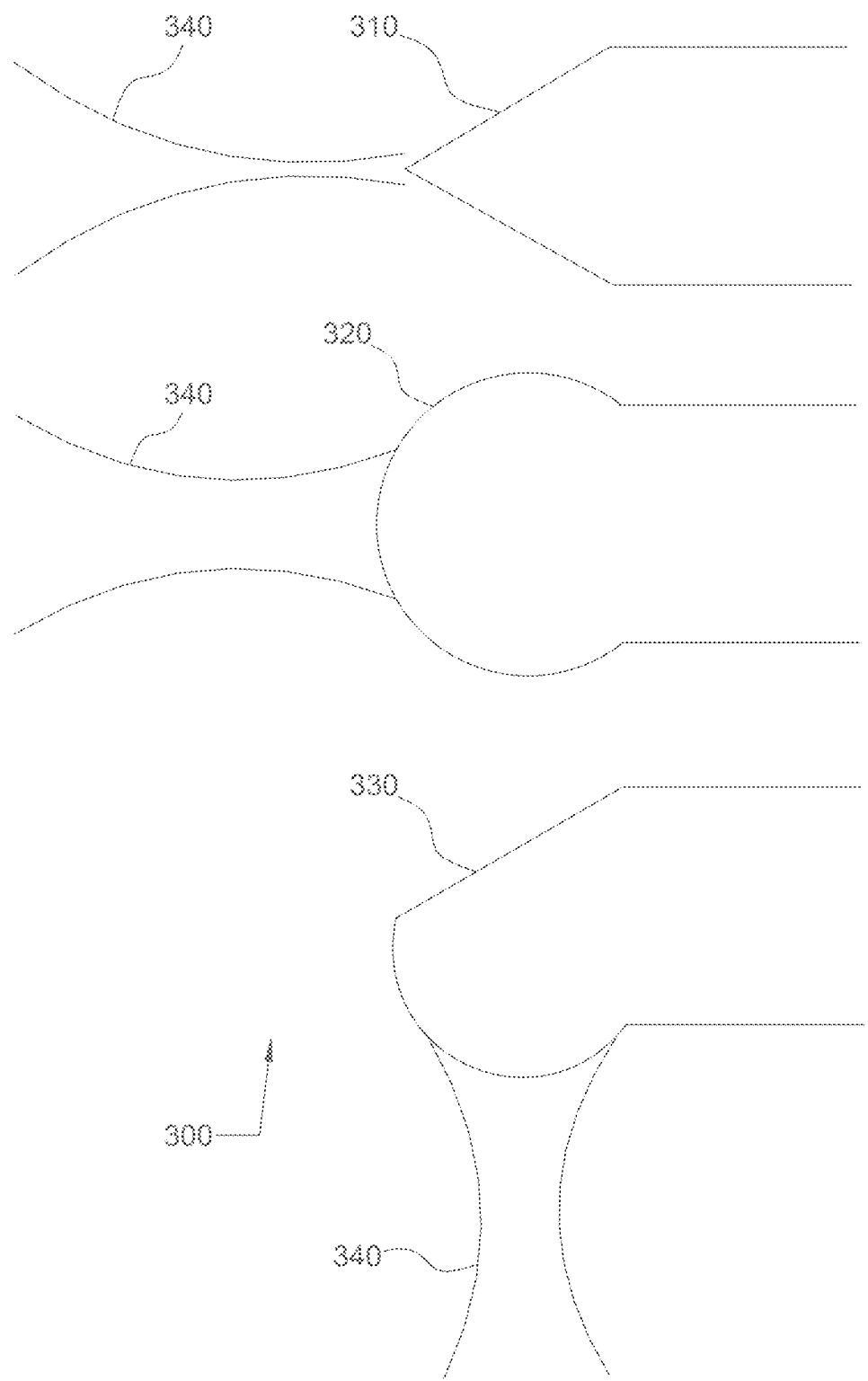
FIG. 3 illustrates several embodiments of a fiber tip shape of an embodiment of the present invention.

Referring to FIG. 3, the optical fiber tip 300 can be shaped in multiple ways. For example, the fiber tip 300 can be shaped in a conical shape 310 to displace tissue radially during penetration with little axial tissue compression, thus reducing damage to the patient. The fiber tip 300 can also be shaped in a ball fashion 320, namely a ball lens, to enable larger light throughput 340 and maximize image sensitivity, or a semi-ball lens for side-firing light. The fiber tip 300 can also be shaped at a special angle 330 to reflect light 340 away from the forward configuration (e.g. side firing configuration).

Figure 4A:
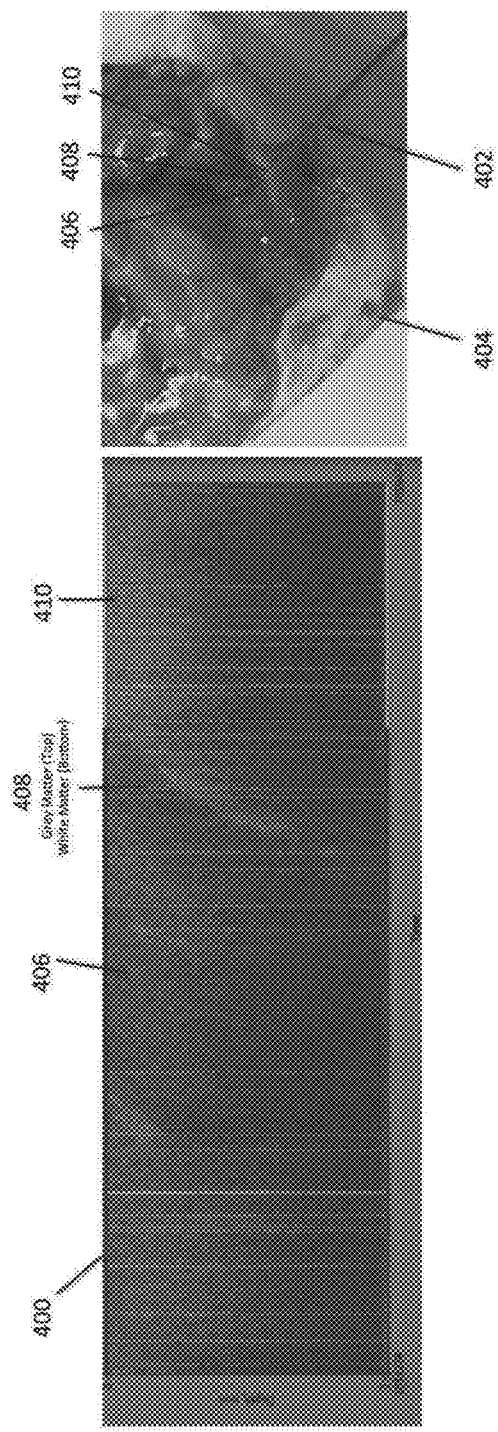
FIG. 4A illustrates OCT contrast in brain for landmarking and target identification.
Figure 4B:
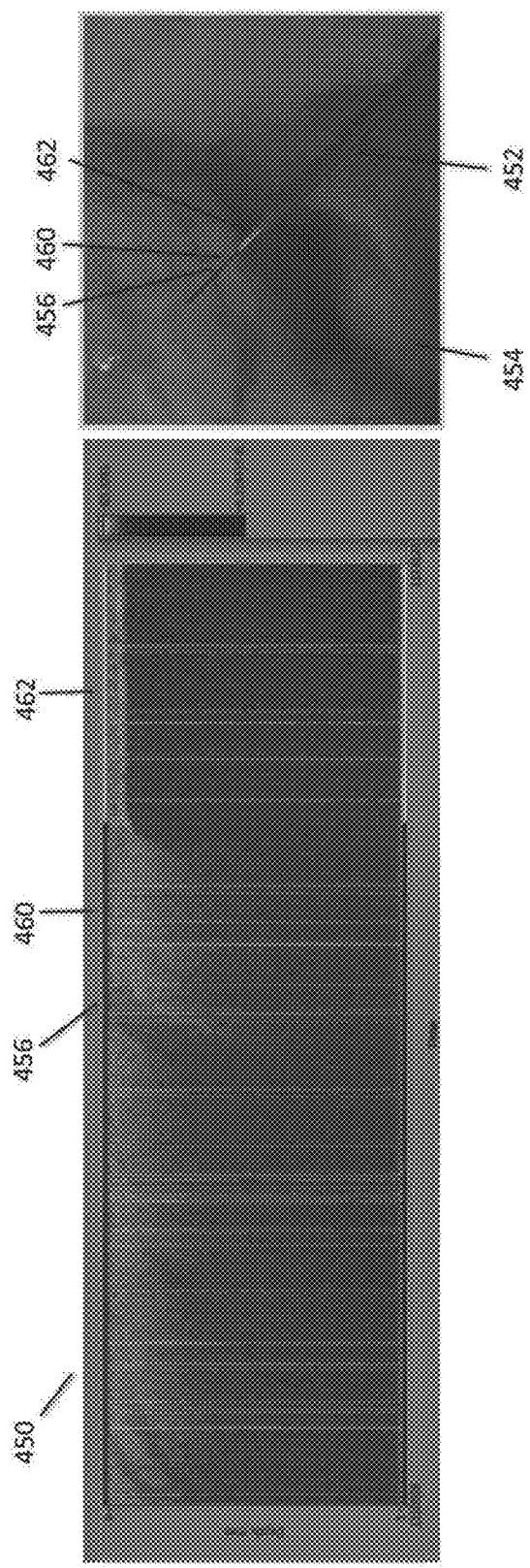
FIG. 4B illustrates a further embodiment of OCT contrast in brain for landmarking and target identification.

Referring to FIG. 4, example images are provided from optical coherence tomography (OCT) contrast in sheep brain. The OCT images are produced using a GRINTech Sidefire probe to acquire an image depth of 1 mm as the probe penetrates sheep brain tissue. FIG. 4A illustrates an OCT image 400 provided by an OCT probe 402 as it penetrates the sheep brain 404. The scatter corresponding to Grey Matter 406, Transition area 408 and White Matter 410 in the sheep brain 404 are indicated above the OCT image 400. FIG. 4B illustrates a further example of an OCT image 450 provided by an OCT probe 452 as it penetrates the sheep brain 454. In this example, scatter as the probe passes through Grey Matter 456, White Matter 460, and a Cavity 462 in the sheep brain 454 are indicated above the OCT image 450.

For guiding placement of a probe through brain tissue, scattering contrast in optical coherence tomography (OCT) and polarization contrast in polarization-sensitive optical coherence tomography (PSOCT) can provide fiber tract contrast, which can be used as landmarks, enabling the surgeon to identify the region of the brain as the probe is penetrating into the brain (Jafri, M. S., et al., Journal of Biomedical Optics 10(5), 051603). For example, OCT images through the STN typically show abundant fine arterioles, whereas OCT images of the substantia nigra typically show thick ribbons of white matter. Thus, a lateral position of a probe track can be inferred from the length through the STN. If the thickness of the STN is about 1 mm, it is the lateral edge of the STN, whereas through the center of the STN the thickness of the STN is about 5 mm. A trajectory that misses the STN and passes through only white matter fails to show the characteristic projection of the STN.

Figure 5A:
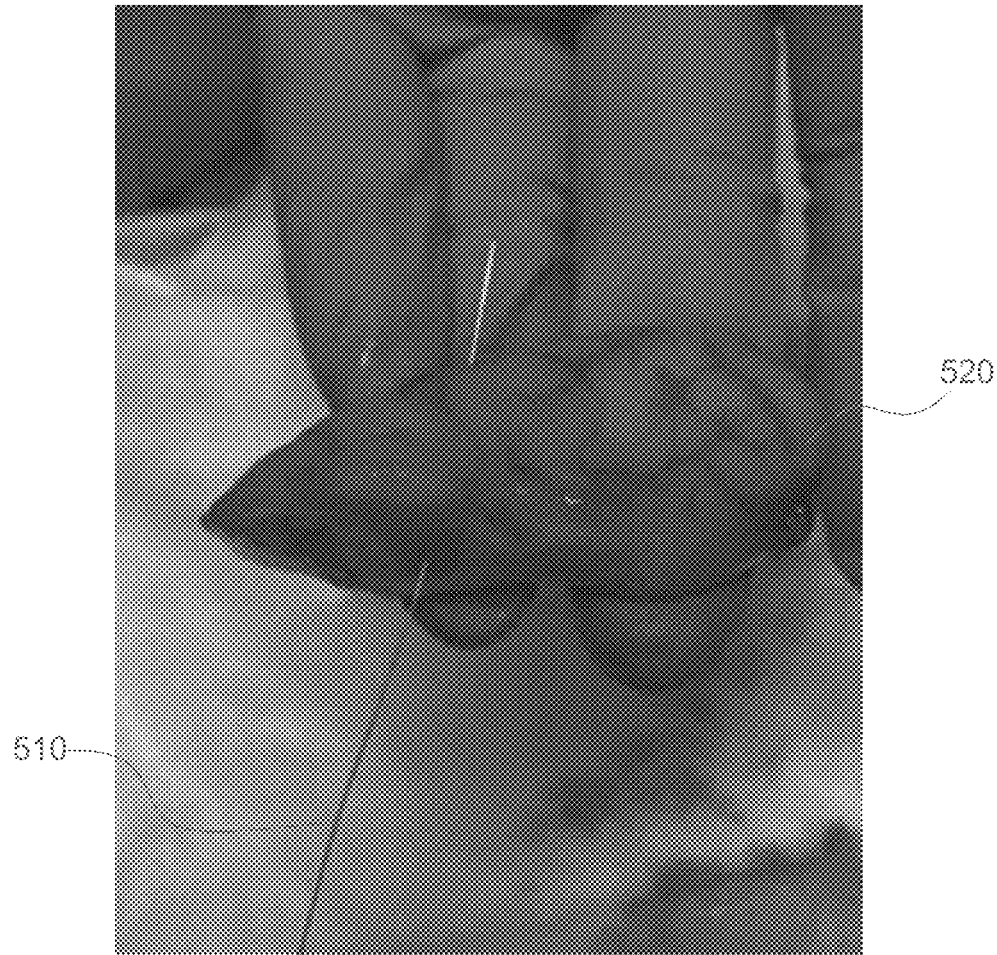
FIG. 5A illustrates an example of metal-coated fiber penetrated through a sheep brain.
Figure 5B:
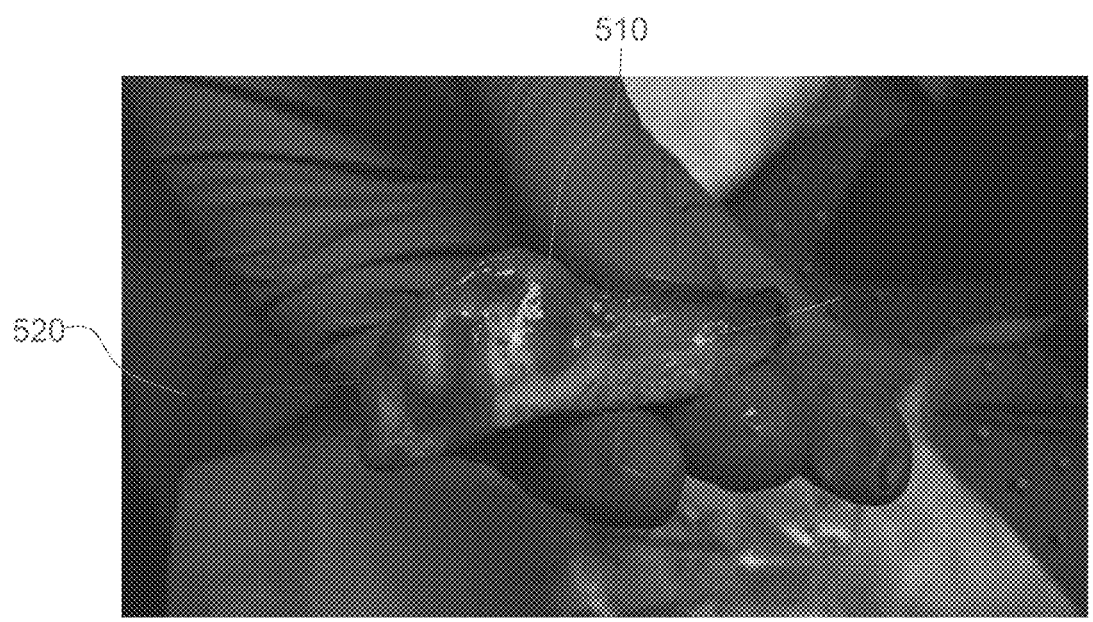
FIG. 5B illustrates a further example of metal-coated fiber penetrated through a sheep brain.
Figure 5C:
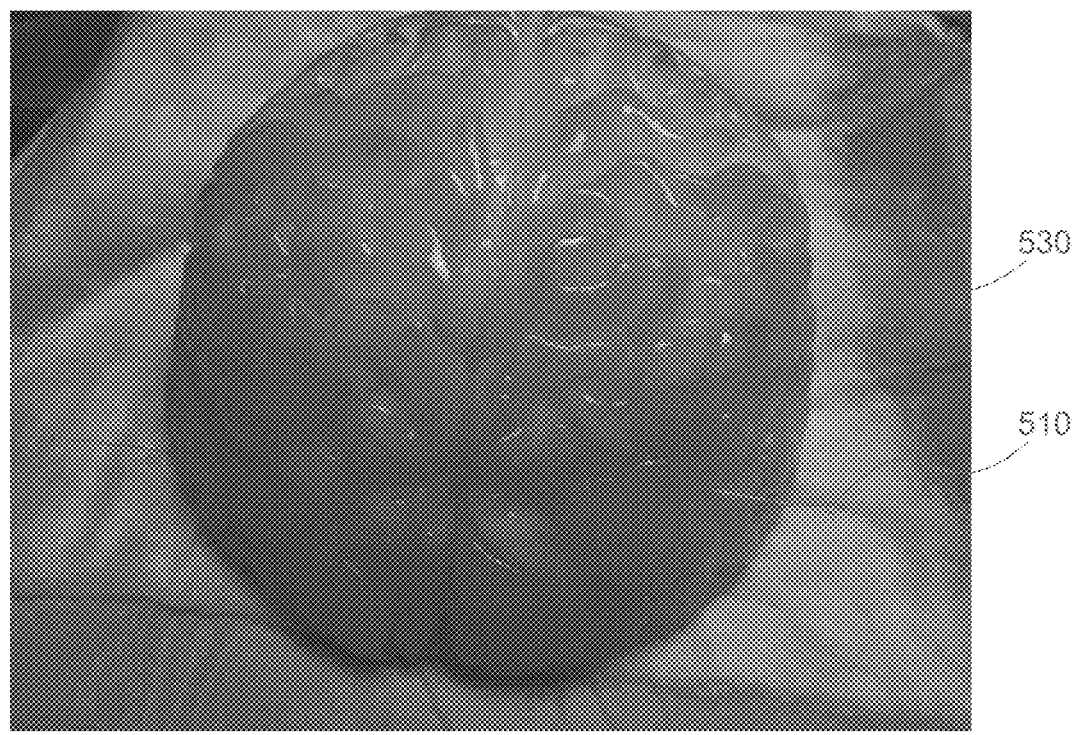
FIG. 5C illustrates an example of metal-coated fiber penetrated through BrightMatter Simulator.
Figure 6:
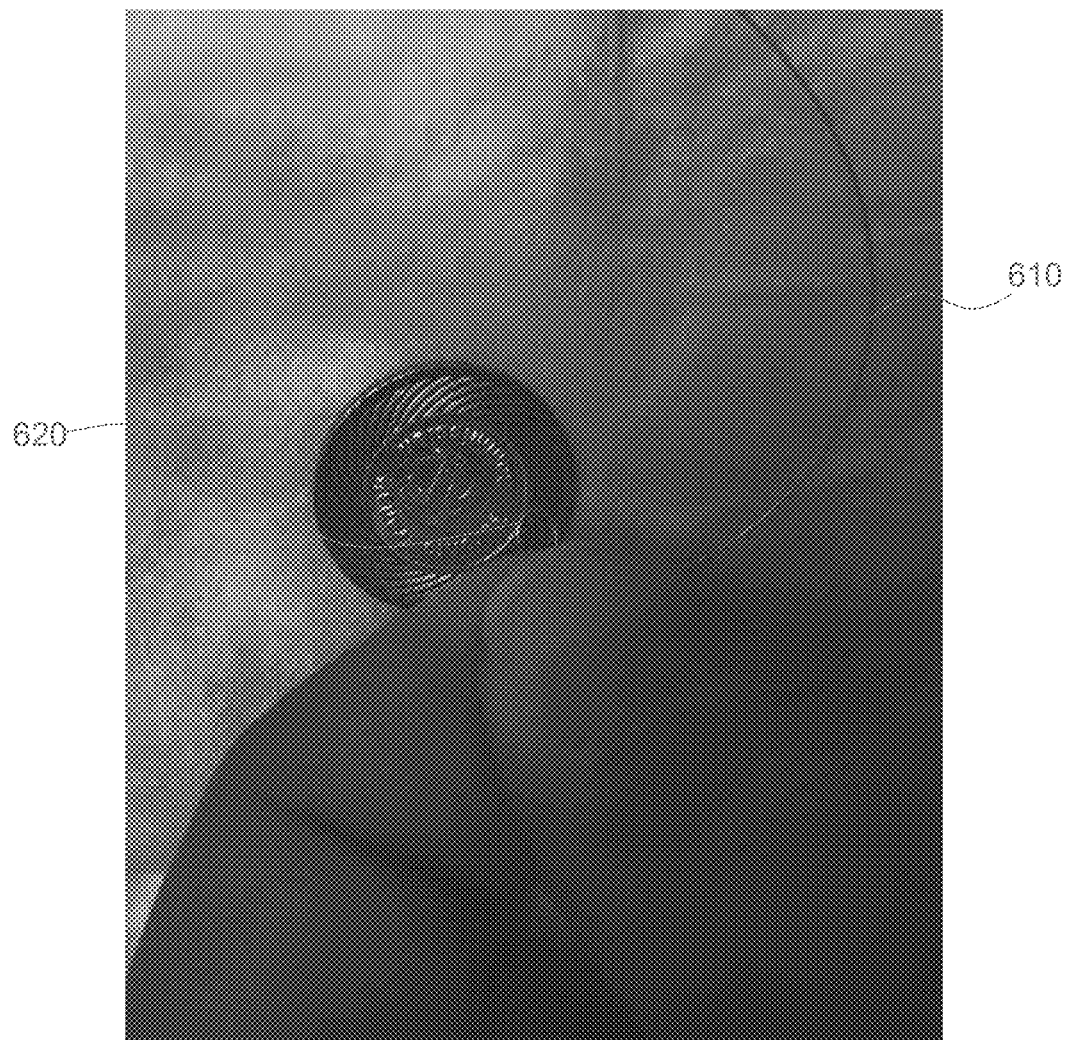
FIG. 6 illustrates an example of metal coated fiber bent to 2 to 3 mm in diameter.
Figure 7A:
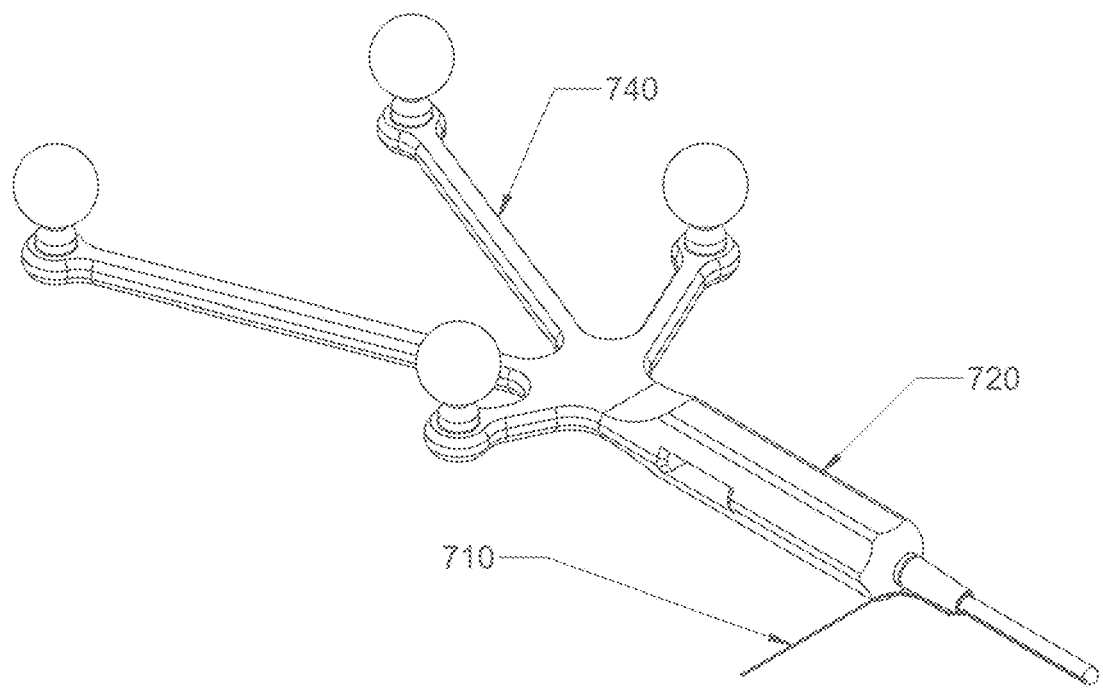
FIG. 7A illustrates an embodiment wherein a probe is attached to a surgical pointer.
Figure 7B:
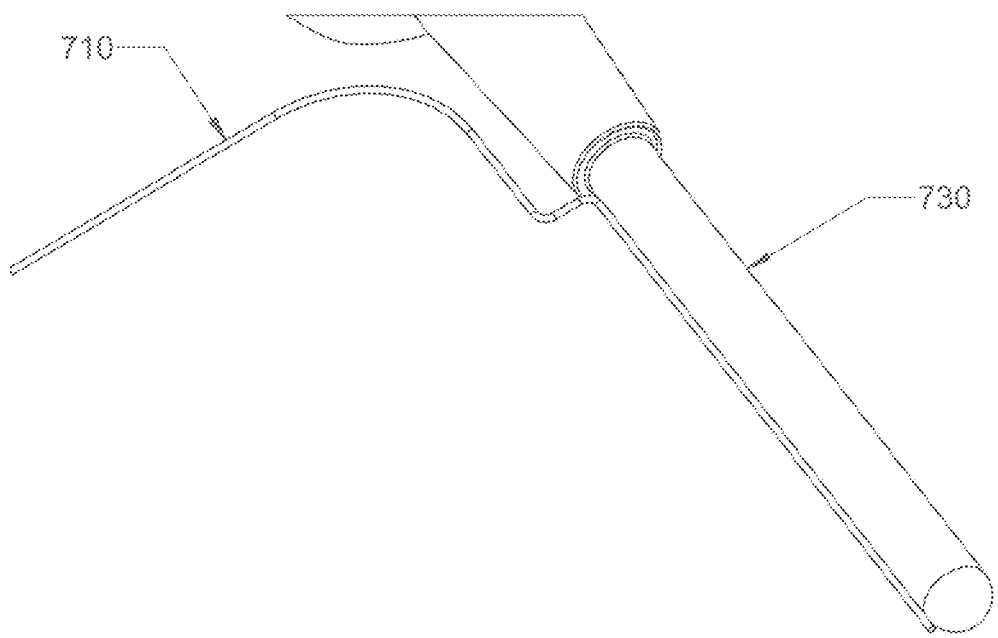
FIG. 7B illustrates a further embodiment wherein a probe is attached to a suction tool.

OCT imaging can provide the following benefits in DBS:
OCT contrast can be used to update registration dynamically intraoperatively
OCT angiography can provide micro-vasculature information as the probe penetrates, which helps the surgeon to avoid bleeding caused by cutting major arteries and veins.
OCT provides very high imaging resolutions (greater than 1 micron) enabling more accurate identification of the targets in millimeter scale.
OCT provides contrast into the tissue non-destructively which helps suggest the direction for lead reinsertion when the target is missed.
Metal coated fibers are sterilizable for use in surgery and in patients
Referring to FIG. 5, metal coated fibers 510 are very strong, enabling the probe to penetrate into brain tissue (in this example sheep brain tissue) 520 or a brain simulator 530 with ease without damage to the fiber.
Referring to FIG. 6, the metal coated fiber 610 is highly flexible 620, in this image easily bent to only 2 to 3 millimeters in diameter.
When a metal coated fiber breaks, it does not break into small pieces
Referring to FIG. 7, an alternate embodiment for the metal-coated optical fiber 710 is to use the probe or the optical portion of the probe with a surgical pointer 720 or a suction tool 730. In this way, as a target tissue is navigated with a pointer 720, the tissue may be imaged dynamically using the optical fiber for OCT contrast and electophysiological recordings made of the surrounding tissue, thus enhancing the ability to map the tissue intraoperatively. Similarly, the probe could be used together with a surgical tool (e.g. suction tool 730 or a pointer tool 720) for optical and electrophysiological recordings to refine the mapping of the instrument within the brain tissue. Use of the probe 710 with either a pointer tool 720 or a suction device 730 may include a tracker tree 740 to allow for tracking the instruments intraoperatively.

The specific embodiments described above have been provided by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A surgical tool for tissue recording in a medical procedure, comprising:
a flexible optical fiber for optical coherence tomography imaging, having an optical fiber distal end, an optical fiber proximal end, and an optical fiber length extending from the optical fiber distal end to the optical fiber proximal end;
an outer insulation coating surrounding the optical fiber length and having at least one portion; and
one of a surgical pointer and a suction tool coupled with the at least one portion of the outer insulation coating,
the flexible optical fiber configured to dynamically image the tissue using at least one of optical coherence tomography contrast and electrophysiological recordings made thereof, and
the optical fiber length comprising a fused silica cladding and a germanium-doped silica core, and
the optical fiber length is split into an optical connector configured to couple with an optical coherence tomography system and into an electrical connector configured to couple with an electro-physiological recording system,
thereby enhancing intraoperatively mapping the tissue, and
thereby facilitating dynamically intraoperatively updating registration using the optical coherence tomography contrast.

2. The surgical tool as in claim 1, further comprising a metal coating surrounding the optical fiber length and surrounded by the outer insulation coating, having a metal coating distal end and a metal coating proximal end,
wherein the insulation coating is discontinuous in proximity to the metal coating distal end, thereby providing contact between the metal coating and the tissue for receiving an electrical signal from the tissue, and
wherein the optical fiber length, surrounded by the metal coating, facilitates simultaneous microelectrode recording and tissue stimulation.

3. The surgical tool as in claim 2, further comprising the electrophysiological recording system coupled with the metal coating proximal end.

4. The surgical tool as in claim 1, wherein the medical procedure comprises deep brain stimulation.

5. The surgical tool as in claim 1, wherein the optical fiber distal end comprises a shaped tip to focus light for facilitating using optical coherence tomography imaging.

6. The surgical tool as in claim 5, wherein the shaped tip comprises one of: a conical shape, a spherical shape, and a semispherical shape.

7. The surgical tool as in claim 1, wherein the optical fiber distal end comprises an angled distal end.

8. The surgical tool as in claim 1, further comprising an optical coherence tomography system coupled with the optical fiber proximal end.

9. The surgical tool as in claim 1, further comprising a tracker tree for intraoperative tracking coupled with one of the surgical pointer and the suction tool.

10. A method for tissue recording, comprising:
providing a surgical tool for tissue recording in a medical procedure, comprising:
providing a flexible optical fiber for optical coherence tomography imaging, having an optical fiber distal end, an optical fiber proximal end, and an optical fiber length extending from the optical fiber distal end to the optical fiber proximal end, providing the optical fiber length comprising providing a fused silica cladding and a germanium-doped silica core, and providing the flexible optical fiber comprising providing the optical fiber length as split into an optical connector configured to couple with an optical coherence tomography system and into an electrical connector configured to couple with an electrophysiological recording system;

providing an outer insulation coating surrounding the optical fiber length and having at least one portion; and providing at least one of a surgical pointer and a suction tool coupled with the at least one portion of the outer insulation coating;

inserting at least one of a surgical pointer and a suction tool, coupled with the at least one portion of the outer insulation coating, into a tissue;

dynamically imaging the tissue, via the flexible optical fiber, using at least one of optical coherence tomography contrast and electrophysiological recordings made thereof, thereby enhancing intraoperatively mapping the tissue, dynamically imaging the tissue comprising:

collecting intraoperative image data through the optical fiber by using optical coherence tomography;

receiving the intraoperative image data on a computer, and displaying an image, corresponding to the intraoperative image data, on a monitor; and dynamically intraoperatively updating registration using the optical coherence tomography contrast.

11. The method of claim 10, further comprising using the intraoperative image data to determine a location in the tissue.

12. The method of claim 10, further comprising receiving an electrical signal from the tissue to a metal coating, having a distal end, surrounding the optical fiber length, through discontinuities in the outer insulation coating proximate the metal coating distal end, thereby providing a contact between the tissue and the metal coating, wherein the optical fiber length, surrounded by the metal coating, facilitates simultaneous microelectrode recording and tissue stimulation.

13. The method of claim 12, further comprising measuring the electrical signal using an electrophysiological recording system.

14. The method of claim 12, further comprising stimulating the tissue using electrical signals from the metal coating to the tissue at the contact between the tissue and the metal coating.

* * * * *